United States Patent [19]

Kaneko et al.

[11] Patent Number: 5,415,990
[45] Date of Patent: May 16, 1995

[54] METHOD OF FORMING SILVER HALIDE PHOTOGRAPHIC CYAN DYE IMAGE

[75] Inventors: Yutaka Kaneko; Rudchenko F. Vladimir; Satoru Ikesu, all of Hino, Japan

[73] Assignee: Konica Corporation, Japan

[21] Appl. No.: 224,254

[22] Filed: Apr. 7, 1994

[30] Foreign Application Priority Data

Apr. 12, 1993 [JP] Japan .................. 5-084709

[51] Int. Cl.$^6$ ........................ G03C 7/38
[52] U.S. Cl. .................. 430/558; 430/384; 430/385
[58] Field of Search ............ 430/558, 384, 385

[56] References Cited

U.S. PATENT DOCUMENTS 3,782,956  1/1974  Boie .................... 430/558
5,223,386  6/1993  Kita et al. ............. 430/558

FOREIGN PATENT DOCUMENTS 386931  9/1990  European Pat. Off. ....... G03C 7/32

Primary Examiner—Lee C. Wright
Attorney, Agent, or Firm—Jordan B. Bierman; Bierman and Muserlian

[57] ABSTRACT

A novel cyan coupler for photographic dye, a process of forming a dye using the coupler and a photographic material containing the cyan coupler are disclosed. The coupler is represented by formula

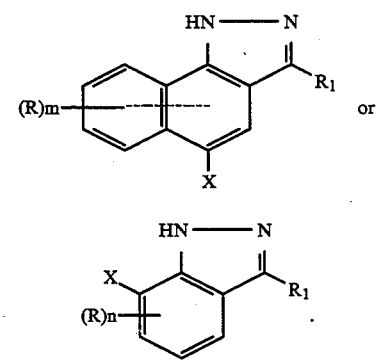

R, $R_1$, X, m and n are defined in the specification.

2 Claims, 1 Drawing Sheet

METHOD OF FORMING SILVER HALIDE PHOTOGRAPHIC CYAN DYE IMAGE

FIELD OF THE INVENTION

The present invention relates to a novel coupler which is used as a material for silver halide light-sensitive color photographic materials. To be more specific, the present invention relates to a novel photographic cyan dye-forming coupler which is capable of forming a dye image with excellent color reproduction property and improved durability against heat and moisture.

BACKGROUND OF THE INVENTION

In general when a color photographic image is produced, after giving an exposure to a silver halide light-sensitive color photographic material, the color photographic material undergoes color development. Then, in the exposed area, oxidized aromatic primary amine color developing agent reacts with a dye-forming coupler, to generate a dye and thus a color image is formed. In this photographic process, color reproduction method using subtractive color system is used, and thereby a color image consisting of yellow, magenta, and cyan dye images is formed.

Heretofore, as the photographic coupler used to form a yellow dye image, for example, acyl acetanilide-type coupler is known. As the coupler for forming a magenta dye image, for instance, pyrazolone, pyrazolobenzimidazole, pyrazolo triazole and indazolone-type couplers are known. And as for the coupler for forming a cyan dye image, phenol or naphthol type coupler is usually used. It is desirable that the dye image obtained from these couplers is not changed or discolored easily, even when it is exposed to light for a long time, or when it is stored under high temperature and high humidity.

However, up to now, in spite of the fact that various researches and developments have been made, the above-mentioned phenol type coupler and naphthol type couplers are still insufficient in view of spectral absorption characteristics and durability against heat and moisture. Various attempts and proposals, aiming at improving these points, including in search of a substituent in the coupler have been made, however, a coupler, which satisfies all these requirements has not been found yet.

A photographic coupler, by which a dye image having excellent spectral absorption characteristics and improved durability against heat and moisture can be obtained, is desired.

SUMMARY OF THE INVENTION

The first object of the present invention is to provide a novel photographic cyan dye-forming coupler which is used as a material for the silver halide light-sensitive color photographic material.

The second object of the present invention is to provide a photographic cyan dye-forming coupler, of which cyan dye image produced therefrom has excellent spectral absorption characteristics and improved durability against heat and moisture.

The cyan coupler of the invention is represented by the Formula I or II.

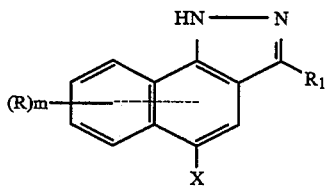

Formula I

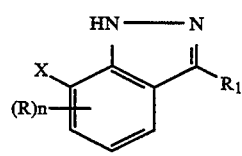

Formula II wherein R represents a substituent, m is an integer from 1 to 5, n is an integer from 1 to 3, R's may be same or different when m or n is more than 2; $R_1$ is an aliphatic group, an aryl group, heterocyclic group, an aliphatic oxy group, an aryloxy group, a heterocyclic oxy group, an acyloxy group, a carbamoyloxy group, a phosphonyloxy group, a carbamoyl group, a sulfamoyl group, an amino group, an acylamino group, an imido group, a sulfonamindo group, a sulfamoyl group, an oxycarbonylamino group or a phosphnylamino group, each of which may have a substituent; X is a hydrogen atom or an atom or a group splitting off on the reaction with an oxidation product of a color developing agent.

DETAILED DISCLOSURE OF THE INVENTION

Figure 1:
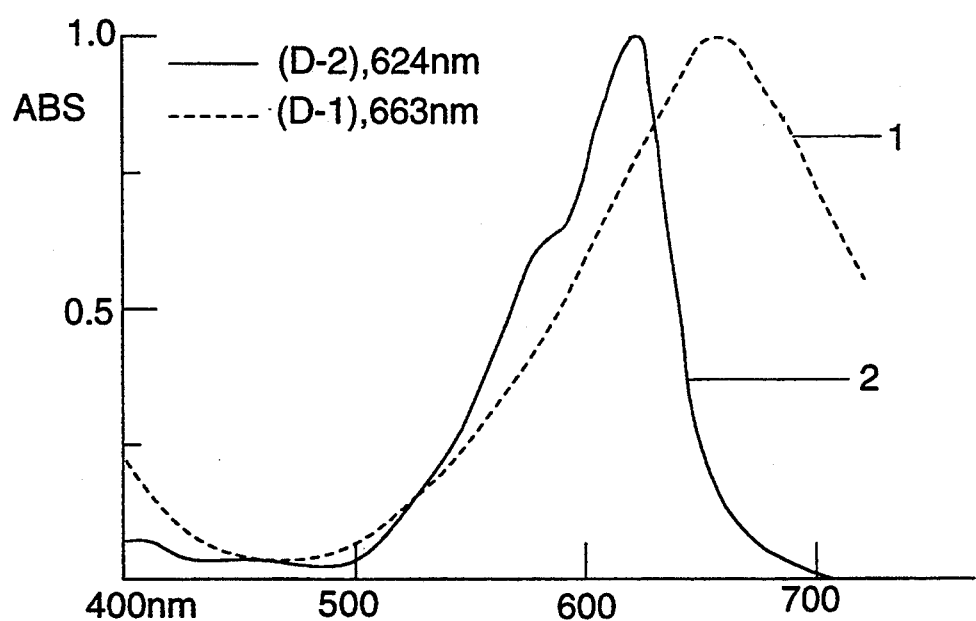
FIG. 1 shows spectroscopic absorption spectra of dyes.
1. Spectroscopic absorption curve of D-1 resulted from a coupler of the invention.
2. Spectroscopic absorption curve of D-2 resulted from a conventional coupler.

In the Formulas I, II there is no special limitation to the substituent represented by R. The substituent R includes, typically, each group of aliphatic, aryl, anilino, acylamino, sulfonamido, alkylthio, arylthio, alkenyl or cycloalkyl. In addition to the above, it further includes, for example, a halogen atom or each group of cycloalkenyl, alkinyl, heterocyclic, sulfonyl, sulfinyl, phosphonyl, acyl, carbamoyl, sulfamoyl, cyano, alkoxy, aryloxy, heterocyclic-oxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, hydroxy, carboxy, or heterocyclic-thio and, besides, a spiro compound residual group or an organic hydrocarbon compound residual group.

The aliphatic group represented by R may be straight-chained or branched and may be saturated or not. The aliphatic group may have a substituent, examples of which includes aryl, anilino, acylamino, sulfonamido, alkylthio, arylthio, alkenyl or cycloalkyl. In addition to the above, it further includes, for example, a halogen atom or each group of cycloalkenyl, alkinyl, heterocyclic, sulfonyl, sulfinyl, phosphonyl, acyl, carbamoyl, sulfamoyl, cyano, alkoxy, aryloxy, heterocyclic-oxy, siloxy, acyloxy, carbamoyloxy, amino, imido, ureido, sulfamoylamino, alkoxycarbonylamino, aryloxycarbonylamino, alkoxycarbonyl, aryloxycarbonyl hydroxy, carboxy, or heterocyclic-thio and, besides, a spiro compound residual group or an organic hydrocarbon compound residual group.

As for the aryl groups phenyl, 1-naphthyl and 2-naphthyl groups are preferred. The acylamino groups include, for example, an alkylcarbonylamino group or an arylcarbonylamino group.

The sulfonamido groups include, for example, an alkylsulfonyl-amino group and an arylsulfonylamino group.

The alkyl components and the aryl components in the alkylthio and the arylthio groups include, for example, a straight-chained or branched alkyl group or phenyl, 1-naphthyl and 2-naphthyl groups aryl groups each of which may have a substituent.

The alkenyl groups represented by R include, preferably, those having 2 to 32 carbon atoms. The cycloalkyl groups represented thereby include, preferably, those having 3 to 12 carbon atoms and, more preferably, those having 5 to 7 carbon atoms. The alkenyl groups may be straight-chained or branched.

The cycloalkenyl groups represented by R include, preferably, those having 3 to 12 carbon atoms and, more preferably, those having 5 to 7 carbon atoms.

The sulfonyl groups represented by R include, for example, an alkylsulfonyl group and an arylsulfonyl group;

The sulfinyl groups represented by R include, for example, an alkylsulfinyl group and an arylsulfinyl group;

The phosphonyl groups represented by R include, for example, an alkyl phosphonyl group, an alkoxy phosphonyl group, an aryloxy phosphonyl group and an aryl phosphonyl group;

The acyl groups represented thereby include, for example, an alkyl carbonyl group and an aryl carbonyl group;

The carbamoyl groups represented thereby include, for example, an alkyl carbamoyl group and an aryl carbamoyl group;

The sulfamoyl groups represented thereby include, for example, an alkyl sulfamoyl group and an aryl sulfamoyl group;

The acyloxy groups represented thereby include, for example, an alkyl carbonyloxy group and an arylcarbonyloxy group;

The carbamoyloxy groups represented thereby include, for example, an alkylcarbamoyloxy group and an arylcarbamoyloxy group;

The ureido groups represented thereby include, for example, an alkylureido group and an arylureido group;

The sulfamoylamino groups represented thereby include, for example, an alkylsulfamoylamino group and an arylsulfamoylamino group;

The heterocyclic groups represented thereby include, preferably, those having 5- to 7-members and, typically, a 2-furyl group, a 2-thienyl group, a 2-pyrimidinyl group and a 2-benzothiazolyl group;

The heterocyclic-oxy groups represented thereby include, preferably, those having a 5- to 7-membered heterocyclic ring and, for example, a 3,4,5,6-tetrahydropyranyl-2-oxy group and a 1-phenyltetrazole-5-oxy group;

The heterocyclic-thio groups represented thereby include, preferably, those having 5- to 7-members and, for example, a 2-pyridylthio group, a 2-benzothiazolylthio group and a 2,4-diphenoxy-1,3,5-triazole-6-thio group;

The siloxy groups represented thereby include, for example, a trimethylsiloxy group, a triethylsiloxy group and a dimethylbutylsiloxy group;

The imido groups represented thereby include, for example, a succinimido group, a 3-heptadecyl succinimido group, a phthalimido group and a glutarimido group;

The spiro compound residual groups represented thereby include, for example, a spiro[3.3]heptane-1-yl; and The organic hydrocarbon bridging compound residual groups represented thereby include, for example, a bicyclo[2.2.1] heptane-1-yl, tricyclo[3.3.1.1$^{37}$]decane-1-yl and 7,7-dimethylbicyclo[2.2.1]heptane-1-yl.

The examples of the aliphatic group represented by $R_1$ include the same one as mentioned for R.

The examples of the aryl group represented by $R_1$ include the same one as mentioned for a substituent of an aliphatic group of R.

The examples of the heterocyclic group represented by $R_1$ include the same one as mentioned for a substituent of an aliphatic group of R.

The examples of the aliphatic group of the aliphatic oxy group, the aryl group of aryloxy group, the heterocyclic group of the heterocyclic oxy group, acyl group of the acyloxy group and the carbamoyl group of the carbamoyloxy group represented by $R_1$ include the same one as mentioned for a substituent of an aliphatic group of R.

The examples of the phosphnyloxy group represented by $R_1$ include an alkylsulphonyloxy, arylsuphonyloxy, alkyloxysulphnyloxy and aryloxyphosphonyloxy group.

The examples of the carbamoyl group and sulfamoyl group represented by $R_1$ include the same one as mentioned for a substituent of an aliphatic group of R.

The amino group represented by $R_1$ may have a substituent and examples of the substituent include an alkyl group or an aryl group.

The examples of the acylamino group, imido group, sulfonamide group and sulfamoyl group represented by $R_1$ include the same one as mentioned for a substituent of an aliphatic group of R.

The examples of the oxycarbamoylamino group represented by $R_1$ include an alkyloxycarbamoylamino and phenyloxycarbamoylamino. The examples of the phosphonylamino group include an alkylphosphonylamino, arylphosphonylamino, alkyloxyphosphonylamino and aryloxyphosphonylamino group.

The preferable examples of R include an aliphatic group, aryl group, acylamino group, sulfonamido group, a halogen atom, an acyl group, carbamoyl group, sulfamoyl group, alkoxy group, acyloxy group, carbamoyloxy group, imido group, ureido group, sulfamoylamino group, alkoxycarbonylamino group, aryloxycarbonylamino group, alkoxycarbonyl group, aryloxycarbonyl group and hydroxy group.

The preferable examples of $R_1$ include an aliphatic group, aryl group, aliphatic-oxy group, acylamino group, imido group, sulfonamido group, sulfamoylamino group, carbamoylamino group, oxycarbonylamino group and phosphonylamino group. The more preferable example of $R_1$ is —NHSO$_2$—Aryl,   —NHSO$_2$—Alkyl,   —NHPO(Aryl)$_2$ or —NHPO(—O—Aryl)$_2$, wherein Aryl is an aryl group which may have a substitutent, Alkyl is an alkyl group which may have a substituent.

The groups capable of splitting off upon reaction with the oxidized product of a color developing agent, which are represented by X, include, for example, a halogen atom (such as a chlorine atom, a bromine atom and a fluorine atom) and each of the groups of alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring bonded with a nitrogen atom, alkyloxycarbonylamino, aryloxycarbonylamino and carboxyl. Among them, halogen atoms, particularly., a chlorine atom, an alkoxy group, an aryloxy group, an alkylthio group and arylthio group are preferable.

The examples of the cyan coupler of the invention is listed.

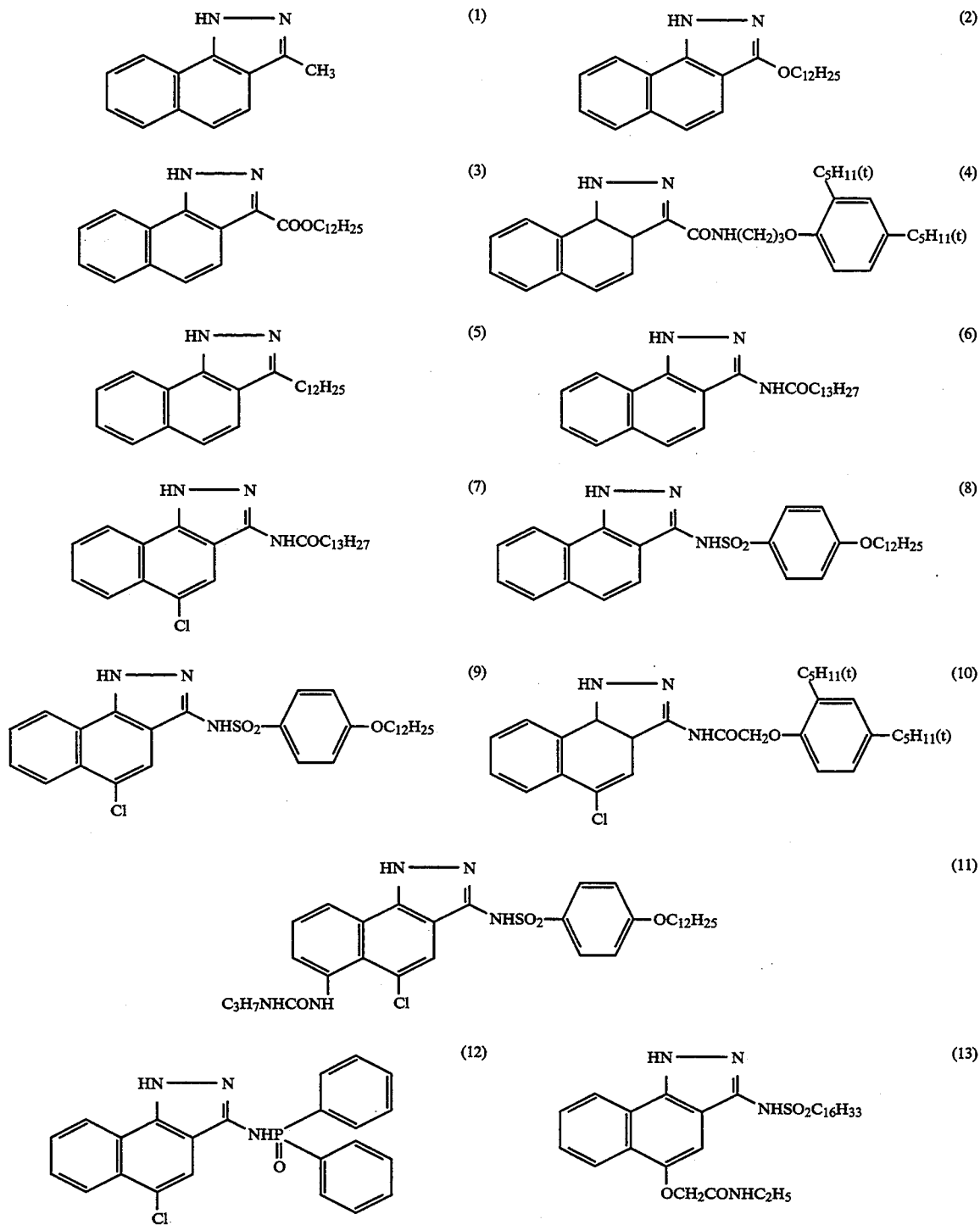

-continued
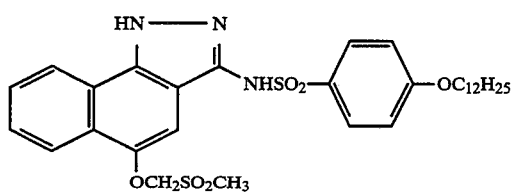 (14)
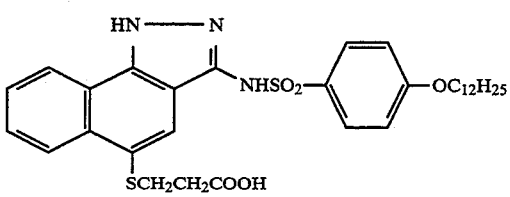 (15)
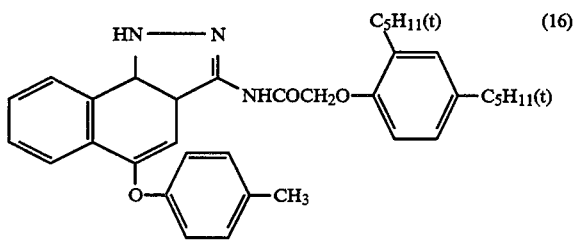 (16)
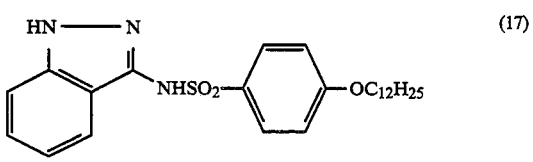 (17)
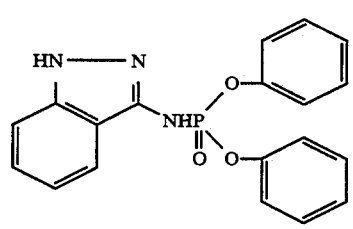 (18)
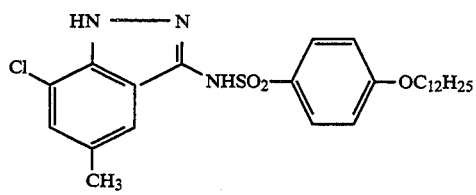 (19)
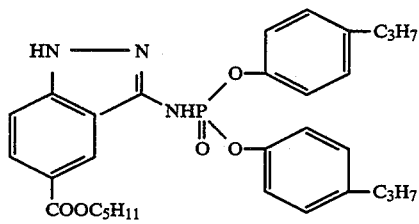 (20)
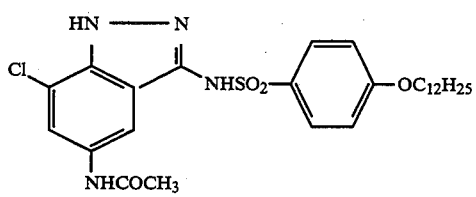 (21)
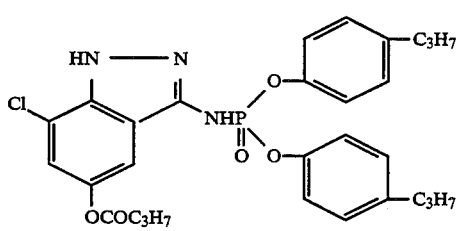 (22)
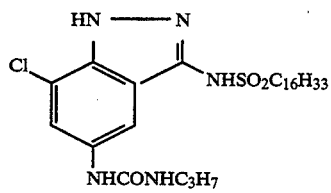 (23)
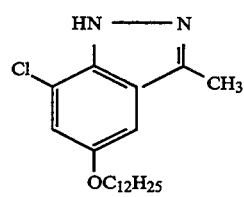 (24)
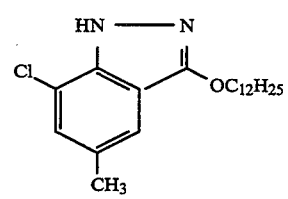 (25)
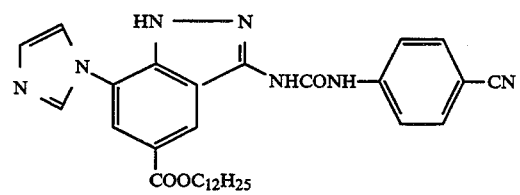 (26)

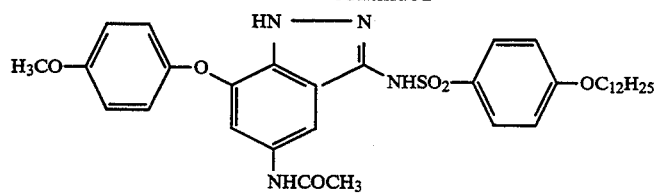

(27)

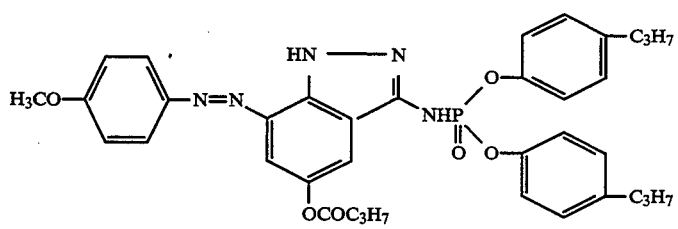

(28)

The preferable examples are couplers 8 to 23, 27 and 28. The most preferable examples are 8, 9, 11 to 15, 17 to 23 and 27.

The cyan coupler of the invention can be synthesized according to J. Am. Chem. Soc., 65, 1804 (1943) and Zh. Org. Khim. 14(5), 1051 (1978).

Synthesis Example will now be given below.

Synthesis Procedures

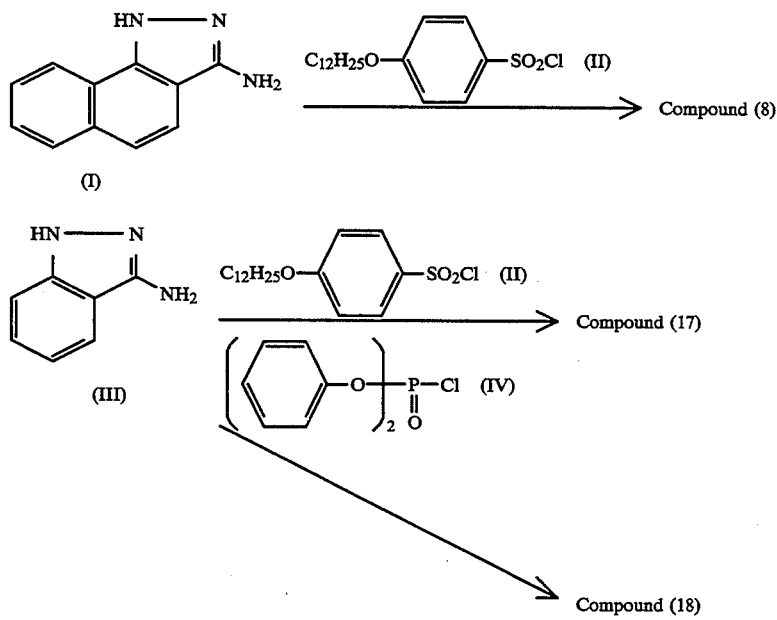

I) Synthesis of Compound (8)

Dissolving 18 g of intermediate (I), that was synthesized according to J. Am. Chem. Soc., 65, 1804 (1943), in 200 ml of pyridine, and the solution was stirred at 10° C. To the solution 36 g of the Intermediate (II) was added for 2 hours. Stirring was continued for 2 hours more after the addition. The resulted liquid was poured into 500 ml of water and was subjected extraction with 400 ml of ethylacetate. The result was washed with water twice and dried with magnesium sulfite anhydride, then ethylacetate was removed by evaporation under educed pressure to obtain pale orange oil. It was purified through column chromatography to obtain 38 g (yield 78%) of pale yellow oil compound (8).

The structure thereof was confirmed by 1HNMR, IR spectral analysis and FD mass-spectral analysis.

II). Synthesis of Compound (17)

Dissolving 13 g of intermediate (III), that was synthesized according to Zh. Org. Khim. 14(5), 1051 (1978), in 150 ml of pyridine, and the solution was stirred at 10° C. To the solution 36 g of the Intermediate (II) was added for 2 hours. Stirring was continued for 2 hours more after the addition. The resulted liquid was poured into 500 ml of water and deposited crystal was filtrated and was recrystallized from 80 % ethanol to obtain 29 g (yield 70 %) of grayish white solid compound (17), having melting point of 158° C.

The structure thereof was confirmed by ¹HNMR, IR spectral analysis and FD mass-spectral analysis.

III). Synthesis of Compound (18)

Dissolving 13 g of intermediate (III), that was synthesized according to Zh. Org. Khim. 14(5), 1051 (1978), in 150 ml of pyridine, and the solution was stirred at 10° C. To the solution 27 g of the Intermediate (IV) was added for 2 hours. Stirring was continued for 2 hours more after the addition. The resulted liquid was poured into 500 ml of water and was subjected extraction with 400 ml of ethylacetate. The result was washed with water twice and dried with magnesium sulfite anhydride, then ethylacetate was removed by evaporation under educed pressure to obtain brown oil. It was purified through column chromatography to obtain 24.5 g (yield 68%) of pale orange oil compound (18).

The structure thereof was confirmed by $^1$HNMR, IR spectral analysis and FD mass-spectral analysis.

A cyan dye is obtained by reacting the cyan coupler with an oxidation product of a color developing agent. A photographic cyan dye image is obtained by developing an imagewise exposed photographic material containing silver salt in the presence of the cyan coupler with a color developer containing a color developing agent. The silver salt includes silver halide and organic silver salt such as silver behenate and silver salt of benztriazole.

The coupler of the invention may usually be used in an amount of $1 \times 10^{-3}$ to 1 mol and, preferably, $1 \times 10^{-2}$ to $8 \times 10^{-1}$ mols per mol of silver halide.

It is also allowed to use the couplers of the invention with other kinds of cyan couplers in combination.

The usual method and techniques used in usual dye forming coupler can be applied to the couplers of the invention.

The coupler of the invention can be used for a color photographic dye forming material of any color developments, for example, coupler in film development method and coupler in developer development method. The coupler can be added into a developer by being dissolved in alkaline aqueous solution or an organic solvent such as alcohol in case that it is used in coupler in developer development method.

The coupler is contained in a photographic material in case that it is used in coupler in film development method. Typically the coupler is mixed with a silver halide emulsion, and the resulted emulsion is coated on a support to form a color photographic material. The coupler of the invention is used for a color photographic material such as a color negative material, color positive material and color print paper.

The light sensitive material such as color printing paper using the coupler of the invention is adopted to a mono-color or multi-color system. In multi-color system, the coupler of the invention may be contained in any layer, usually, in red sensitive silver halide emulsion layer. The multi-color material comprises three dye image forming units having each spectrum sensitivity of three primary colors. Each of the dye forming unit is composed of a single or multi-layer silver halide emulsion layer having a sensitivity in certain spectrum range. The component layer including the dye image forming layer is arranged in various order as known in the technical field. Typical multi-color light sensitive material comprises a cyan dye forming component unit composed of at least one red sensitive silver halide emulsion layer containing at least one of a cyan coupler wherein at least one of the cyan coupler is the coupler of the present invention, a magenta dye forming component unit composed of at least one green sensitive silver halide emulsion layer containing at least one of a magenta coupler and a yellow dye forming component unit composed of at least one blue sensitive silver halide emulsion layer containing at least one of a yellow coupler, provided on a support.

The light sensitive material may have an additional layer such as a filter layer, an inter layer, a protective layer and a subbing layer. The coupler is allowed to be incorporated in the emulsion layer according to known method. After the coupler of the invention is dissolved with a high boiling point solvent having a boiling point of more than 175° C. or a low boiling point solvent such as butyl acetate or butyl propionate singly or in combination if necessary, the dissolved coupler is mixed with a gelatin aqueous solution containing a surfactant, then it is emulsified by means of high speed mixer or colloid mill, and the emulsified coupler is added to a sliver halide emulsion to prepare a silver halide emulsion.

The silver halides preferably used in the invention are comprised of silver chloride, silver chlorobromide or silver chloroiodobromide and, further, they may also be comprised of a combined mixture such as the mixture of silver chloride and silver bromide. Since extra high developing speed is required in case that the silver halide emulsion is adopted to a color printing paper, the emulsion preferably contains silver chloride as a silver halide component, and the emulsion is preferably a silver chloride, silver bromochloride or silver iodobromochloride each of which contains at least 1% of silver chloride.

The silver halide emulsion is chemically sensitized in a conventional way. It may be also sensitized optically at a desired wave length.

To the silver halide emulsion compounds known as an anti-foggant or a stabilizer is added for the purpose of avoiding fogging and/or keeping the photographic characteristics stable during the preparation or storage of the photographic material, or the developing process.

The color photographic material containing a coupler of the invention may be allowed to use, for example, an anti-color fogging agent, a dye image stabilizer, a UV absorbent, an anti-static agent, a matting agent and a surfactant. The reference is made to the disclosure of, for example, Research Disclosure, No. 176, 22–31 (December, 1978).

The color photographic material comprising a coupler of the invention is processed by color developing process known in the art to form an image.

The color photographic material comprising a coupler of the invention may contain a color developing material as itself or a precursor thereof in a hydrophilic colloidal layer to allow the material processed with an alkaline activating bath.

The color photographic material comprising a coupler of the invention is bleached, fixed after the color development. The bleaching process can be made simultaneously with fixing.

After the fixing processing water washing is undergone after the fixing processing usually. The stabilization may be conducted as a substituted to water washing, or in combination with water washing.

EXAMPLES

The invention will be detailed with reference to the examples. The embodiments of the invention is not limited thereto.

Example 1

On a paper support laminated with polyethylene on both side thereof, each of the layers having the compositions shown below were coated in order to prepare a red sensitive color photographic material 1. The amount is shown as an amount per 1 m$^2$ as far as defined otherwise. The amount of silver halide is shown as an amount converted to silver.

The first layer: An emulsion layer

A layer composed of 1.3 g of gelatin, 0.21 g of a red sensitive silver chlorobromide emulsion (containing silver chloride 99.5 mol%) and a $9.1\times10^{-4}$ mol of comparative coupler (a) dissolved in 0.45 g of dioctylphthalate.

The second layer: A protective layer

A protect layer containing 0.50 g of gelatin. A hardening agent sodium 2, 4-dichloro-5-hydroxy-s-triazine in an amount of 0.017 g for 1 g of gelatin.

Samples of the invention 2 to 8 were prepared by using couplers of the invention in place of the comparative coupler (a) with the same mol.

The resulted samples were processed by the following steps after wedgewise exposure in the normal way.

The processing steps and condition.

| Processing step | Temperature | Time |
| --- | --- | --- |
| Color developing | 35.0 ± 0.3° C. | 45 sec |
| Bleach-fixing | 35.0 ± 0.5° C. | 45 sec |
| Stabilizing | 30 to 34° C. | 90 sec |
| Drying | 60 to 80° C. | 60 sec |
| Color developer | | |
| Deionized water | | 800 cc |
| Triethanol amine | | 10 g |
| N,N-diethyl hydroxyl amine | | 5 g |
| Potassium bromide | | 0.02 g |
| Potassium chloride | | 2.0 g |
| Potassium sulfite | | 0.3 g |
| 1-hydroxyethylidene-1,1-diphosphoric acid | | 1.0 g |
| Ethylenediamine tetraacetic acid | | 1.0 g |
| Catechol-3,5-diphosphonic acid 2 sodium | | 1.0 g |
| Diethylene glycol | | 10 g |
| N-ethyl-N-b-methanesulfonamidoethyl-3-methyl-4-aminoaniline sulfate | | 4.5 g |
| Fluorescent whitening agent, (a 4,4′-diaminostilbene sulfonic acid derivative) | | 1.0 g |
| Potassium carbonate | | 27 g |
| Add water to make in total of 1000 cc | | |
| Adjust pH values of the tank solution to be 10.0. | | |
| Bleach-fixer | | |
| Ferric ammonium ethylenediamine tetraacetate, dehydrate | | 60 g |
| Ethylenediaminetetraacetic acid | | 3 g |
| Ammonium thiosulfate (in an aqueous 70% solution) | | 100 ml |
| Ammonium sulfite (in an aqueous 40% solution) | | 27.5 ml |

Add water to make in total of 1 liter and adjust pH with potassium carbonate or glacial acetic acid to pH 5.7.

| Stabilizer | |
| --- | --- |
| 5-chloro-2-methyl-4-isothiazoline-3-one | 0.2 g |
| 1,2-benzisothiazolin-3-on | 0.3 g |
| Ethylene glycol | 1.0 g |
| 1-hydroxyethylidene-1,1-diphosphonic acid | 2.0 g |
| o-phenyl phenol sodium | 1.0 g |
| Ethylenediaminetetraacetic acid | 1.0 g |
| Ammonium hydroxide (in an aqueous 20% solution) | 3.0 g |
| Fluorescent whitening agent (a 4,4′-diaminostilbene sulfonic acid derivative) | 1.5 g |

Add water to make in total of 1 liter and adjust pH with sulfuric acid or potassium hydroxide to pH 7.0.

The color densities of the processed samples were measured with a densitometer (KD-7, product of Konica Corporation), and the samples were measured after standing for 14 days in a high temperature and high humidity circumstances of 60° C. and 80 % RH to test the fastness against heat and moisture.

The result is shown below. The fastness against heat and moisture is presented by means of the ratio of residual dye at the initial density of 1.0.

Comparative cyan coupler (a) is shown.

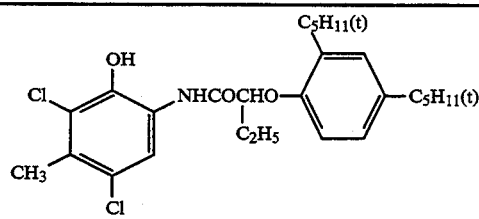

| Sample No. | Coupler | Fastness to heat and moisture (Ratio of residual dye in %) |
| --- | --- | --- |
| 1 | Comparative (a) | 61 |
| 2 | Exemplified (8) | 89 |
| 3 | Exemplified (9) | 87 |
| 4 | Exemplified (12) | 90 |
| 5 | Exemplified (13) | 92 |
| 6 | Exemplified (14) | 88 |
| 7 | Exemplified (19) | 86 |
| 8 | Exemplified (21) | 89 |

The result illustrates the samples using couplers of the invention have high residual dye ratio and are advantageous in heat fastness and moisture fastness comparing with the sample using the comparative coupler.

Example 2

On a subbed triacetylcellulose film support each of the layers having the compositions shown below were coated in order to prepare a red sensitive color reversal photographic material Samples 9 to 14.

The first layer: An emulsion layer

A layer composed of 1.4 g of gelatin, 0.5 g of a red sensitive silver chlorobromide emulsion (containing silver chloride 96 mol%) and $9.1\times10^{-4}$ mol of coupler listed in table 3 dissolved in 1.5 g of dibutylphthalate.

The second layer: A protective layer

A protect layer containing 0.50 g of gelatin. A hardening agent sodium 2,4-dichloro-5-hydroxy-s-triazine in an amount of 0.017 g for 1 g of gelatin.

The resulted samples were processed by the following steps after wedgewise exposure in the normal way.

The processing steps and condition.

| Processing step | Temperature | Time |
| --- | --- | --- |
| First developing | 38° C. | 6 min |
| Washing with water | 38° C. | 2 min |
| Reversing | 38° C. | 2 min |
| Color developing | 38° C. | 6 min |
| Adjustment | 38° C. | 2 min |
| Bleaching | 38° C. | 6 min |
| Fixing | 38° C. | 4 min |
| Washing with water | 38° C. | 4 min |
| Stabilizing | Room temperature | 1 min |
| Drying | | |
| Composition of the processing liquid First Development | | |
| Sodiumtetrapoyphosphate | | 2.0 g |
| Sodium sulfite | | 20.0 g |
| Hydroquinone monosulfate | | 30.0 g |
| Sodium carbonate (monohydrate) | | 30.0 g |
| 1-phenyl-4-methyl-4-hydroxymethyl-3-pyrazolidone | | 2.0 g |

| | |
|---|---|
| Potassium bromide | 2.5 g |
| Potassium thiocyanate | 1.2 g |
| Potassium iodide (0.1% aqueous solution) | 2 ml |
| Water to make | 1000 ml |
| Reversing | |
| Hexasodium nitrilotrimethylenephosphonate | 3.0 g |
| Tin chloride (Dihydrate) | 1.0 g |
| p-Aminophenol | 0.1 g |
| Sodium hydroxide | 5.0 g |
| Glacial acetic acid | 15 ml |
| Water to make | 1000 ml |
| Color developer | |
| Sodiumtetrapolyphosphate | 2.0 g |
| Sodium sulfite | 7.0 g |
| Tertiarysodiumphosphate (undecahydrate) | 36.0 g |
| Potassium bromide | 1.0 g |
| Potassium iodide (0.1% aqueous solution) | 90 ml |
| Sodium hydroxide | 3.0 g |
| Citrazinic acid | 1.5 g |
| N-ethyl-N-beta-methanesulfonamidoethyl-3-methyl-4-aminoaniline sulfate | 11.0 g |
| Ethylenediamine | 3.0 g |
| Water to make | 1000 ml |
| Adjustment | |
| Sodium sulfite | 12.0 g |
| Sodiumetylenediaminetetraacetate (Dihydrate) | 8.0 g |
| Thioglycerin | 0.4 ml |
| Glacial acetic acid | 3 ml |
| Water to make | 1000 ml |
| Bleaching | |
| Sodium ethylenediamine tetraacetate (Dihydrate) | 2.0 g |
| Ferric ammonium ethylenediamine tetraacetate, dihydrate | 120 g |
| Potassium bromide | 100.0 g |
| Water to make | 1000 ml |
| Fixer | |
| Ammonium thiosulfate | 80.0 g |
| Sodium sulfite | 5.0 g |
| Sodium bisulfite | 5.0 g |
| Water to make | 1000 ml. |
| Stabilizer | |
| Formalin (37 wt %) | 5 ml |
| Konidux (produced by Konica Corporation) | 5 ml |
| Water to make | 1000 ml. |

Fastness of the dye image to heat and moisture of the processed samples were evaluated as in the samples of Example 1. The result is shown below.

| Sample No. | Coupler | Fastness to heat and moisture (Ratio of residual dye in %) |
|---|---|---|
| 9 | Comparative (a) | 59 |
| 10 | Exemplified (4) | 87 |
| 11 | Exemplified (10) | 89 |
| 12 | Exemplified (13) | 90 |
| 13 | Exemplified (22) | 86 |
| 14 | Exemplified (27) | 88 |

The result illustrates the samples using couplers of the invention have high residual dye ratio and are advantageous in heat fastness and moisture fastness comparing with the sample using the comparative coupler.

Example 3

On a polyethyleneterephthalate film support a heat developable light sensitive layers having the compositions shown below per 1 m² were coated in order to prepare a heat developable light sensitive photographic material Sample.

| | |
|---|---|
| Benztriazole silver | 0.6 g |
| Gelatin | 3.0 g |
| Reducing agent (*1) | 0.97 g |
| Coupler (18) | 1.0 g |
| Silver iodobromide | 0.45 g |
| Polyvinyl pyrrolidone | 1.0 g |
| Benztriazole | 0.02 g |
| Restrainer (*2) | 0.001 g |
| Heat solvent (*3) | 4.5 g |

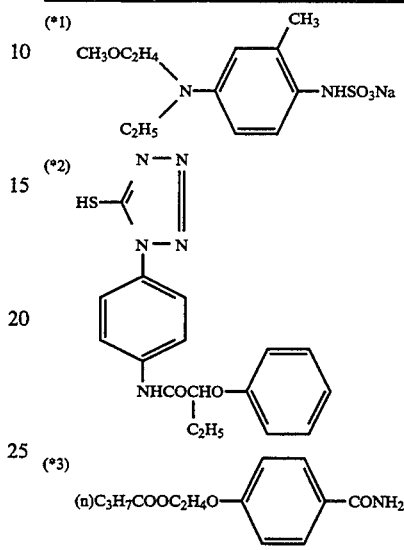

After the imagewise exposure to light the photographic material was superposed onto a receiving material prepared by coating polyvinyl chloride on baryta paper for photographic use, they were developed at 150° C. for 1 min to obtain a good transferred cyan dye image on a receiving material.

Example 4

FIG. 1 shows a spectroscopic absorption spectrum of an azomethine dye D-1 resulted from the coupler (8) of the invention and an indoaniline dye D-2 resulted from the comparative Coupler (a) in methanol solvent. The numeric number 1 denotes a spectroscopic absorption curve of D-1 and number 2 D-2. The longitudinal axis shows absorbance and the lateral axis shows a wave length.

As apparent from the FIG. 1, dye D-1 obtained from a coupler of the invention has a reduced subsidiary absorption at 400 to 500 nm and sharpened primary absorption.

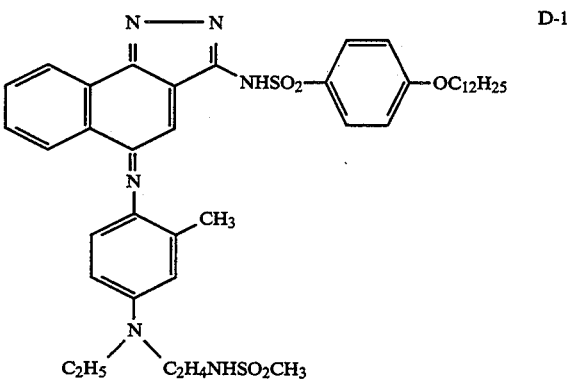

-continued

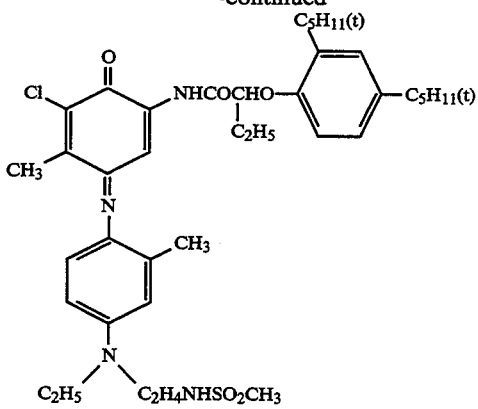

D-2

A cyan dye image formed of a coupler of he invention is excellent in spectroscopic absorption characteristics and durable to heat, and moisture. The coupler of the invention is useful as a dye providing material for the heat developable light sensitive material.

We claim:

1. A color photographic material comprising a light sensitive layer containing silver salt and a coupler provided on a support wherein the coupler is represented by Formula I or II,

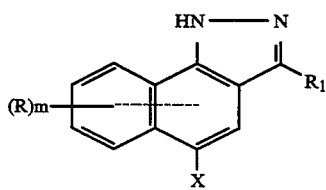
Formula I

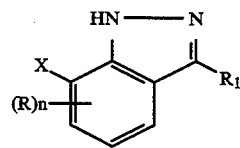
Formula II wherein R represents a substituent, m is an integer from 1 to 5, n is an integer from 1 to 3, R's may be same or different when m or n is more than 2; $R^1$ is an aliphatic group, an aryl group, heterocyclic group, an aliphatic oxy group, an aryloxy group, a heterocyclic oxy group, an acyloxy group, a carbamoyloxy group, a phosphonyloxy group, a carbamoyl group, a sulfamoyl group, an amino group, an acylamino group, an imido group, a sulfonamido group, a sulfamoyl group, an oxycarbonylamino group or a phosphnylamino group, each of which may have a substituent; X is a hydrogen atom or an atom or a group splitting off on the reaction with an oxidation product of a color developing agent.

2. A color photographic material comprising a light sensitive layer containing silver halide and a coupler provided on a support wherein the coupler is represented by Formula I or II,

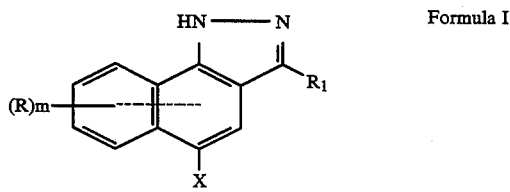
Formula I

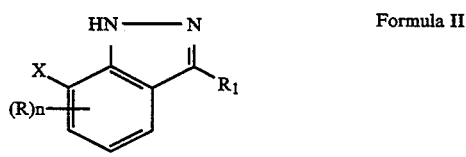
Formula II wherein R represents a substituent, m is an integer from 1 to 5, n is an integer from 1 to 3, R's may be same or different when m or n is more than 2; $R^1$ is an aliphatic group, an aryl group, heterocyclic group, an aliphatic oxy group, an aryloxy group, a heterocyclic oxy group, an acyloxy group, a carbamoyloxy group, a phosphonyloxy group, a carbamoyl group, a sulfamoyl group, an amino group, an acylamino group, an imido group, a sulfonamido group, a sulfamoyl group, an oxycarbonylamino group or a phosphnylamino group, each of which may have a substituent; X is a hydrogen atom or an atom or a group splitting off on the reaction with an oxidation product of a color developing agent.

* * * * *